(12) United States Patent
Kundalgurki

(10) Patent No.: US 7,319,223 B2
(45) Date of Patent: Jan. 15, 2008

(54) METHOD AND APPARATUS FOR CHARACTERIZING A RECESS LOCATED ON A SURFACE OF A SUBSTRATE

(75) Inventor: Srivatsa Kundalgurki, Dresden (DE)

(73) Assignee: Infineon Technologies AG, Munich (DE)

( * ) Notice: Subject to any disclaimer, the term of this patent is extended or adjusted under 35 U.S.C. 154(b) by 646 days.

(21) Appl. No.: 10/940,490

(22) Filed: Sep. 14, 2004

(65) Prior Publication Data

US 2006/0054812 A1   Mar. 16, 2006

(51) Int. Cl.
*G01N 23/00*   (2006.01)
(52) U.S. Cl. .................... 250/306; 250/309; 250/308; 250/310
(58) Field of Classification Search ............... 250/306, 250/309, 308, 310
See application file for complete search history.

(56) References Cited

U.S. PATENT DOCUMENTS

| | | | |
|---|---|---|---|
| 6,337,479 B1 * | 1/2002 | Kley | 250/234 |
| 6,353,219 B1 * | 3/2002 | Kley | 250/234 |
| 6,861,648 B2 * | 3/2005 | Kley | 250/306 |
| 6,880,388 B1 * | 4/2005 | Kley | 73/105 |
| 6,923,044 B1 * | 8/2005 | Kley | 73/105 |
| 7,109,482 B2 * | 9/2006 | Kley | 250/306 |

* cited by examiner

*Primary Examiner*—Lisa Caputo
*Assistant Examiner*—Michael Maskell
(74) *Attorney, Agent, or Firm*—Patterson & Sheridan, L.L.P.

(57) ABSTRACT

Method and apparatus for characterizing a recess located on a surface of a substrate are provided. One embodiment of the invention provides a method for characterizing a recess located on a surface of a substrate. In a first step, a measurement tip is positioned directly above the recess. Subsequently, an electrically conductive path is provided between the measurement tip and the bottom of the recess by ionizing a medium located in the recess. A voltage is applied between the measurement tip and the substrate to measure a current flowing between the measurement tip and the bottom of the recess. The recess is characterized on the basis of the magnitude of the measured current. Another embodiment of the invention provides an apparatus for performing the method for characterizing a recess.

25 Claims, 2 Drawing Sheets

METHOD AND APPARATUS FOR CHARACTERIZING A RECESS LOCATED ON A SURFACE OF A SUBSTRATE

BACKGROUND OF THE INVENTION

1. Field of the Invention

The present invention relates to a method and an apparatus for characterizing a recess located on a surface of a substrate.

2. Description of the Related Art

Currently, electronics is dominated by microelectronic semiconductor components with integrated circuits. Such integrated circuits include a complex arrangement of electronic structures which are disposed and interconnected with each other on tiny semiconductor substrates, also called chips. The combined production of integrated circuits on a semiconductor disc, also referred to as wafer, is characterized by a large number of successive process steps.

One main demand of the semiconductor industry is the continuous power enhancement provided by increasingly faster integrated circuits which is interrelated to a miniaturization of the electronic structures. In the course of this development, the semiconductor industry has changed over to producing increasingly three-dimensional structures with minimal lateral dimensions on the semiconductor wafers which require less space on the surfaces of the semiconductor chips. In general, recesses or vias located on the surfaces of the wafers serve as initial structures for the three-dimensional structures. Such recesses are typically produced by subjecting the wafers to specific photolithographic and etch processes.

The miniaturization of the electronic structures correlates to an increasing accuracy of the production processes. At the same time, accurate and reliable inspection procedures are required in order to control the production processes. With regard to three-dimensional structures, methods and devices for characterizing recesses located on the surfaces of the wafers have a great significance, as these methods make it possible to find out unwanted deviations from structure dimensions or defects, which may be due to incorrect production processes and which may affect the operability of produced semiconductor chips.

One of the currently used methods for characterizing recesses located on a surface of a wafer is based on the usage of a scanning electron microscope (SEM). For this method, the respective wafer is broken in the area of the recesses of interest and positioned in a vacuum chamber. Afterwards, the waste edge of the wafer is hit or scanned by a focused electron beam such that secondary electrons are knocked loose and emitted from the waste edge. The secondary electrons are collected by a detector in order to build up an image of the waste edge. Thus, for example, a depth of a recess may be characterized or an unwanted insulating or residue layer located at the bottom of a recess due to an incomplete etch process may be detected.

A drawback of this method is that the wafer is destroyed by the breakage. As a consequence, the method is very costly. Moreover, the method may only be applied offline to a few wafers and in particular, not to the product wafers in the production line. Accordingly, the results of the offline measurement may not be necessarily representative of measurements on product wafers.

In an alternative method for characterizing recesses located on the surface of a wafer, an atomic force microscope (AFM) is used. An atomic force microscope operates by scanning the surface of interest with a microscope tip which is fixed to a cantilever. By measuring attractive or repulsive interatomic forces between the tip and the surface of the wafer being inspected, topographical information on the surface and thus information on the lateral dimensions and the depth of a recess may be derived.

In order to decipher the depth of a recess, the microscope tip has to be sufficiently small so as to traverse the bottom of the recess. Due to the shrinking lateral dimensions of the structures and thus of the recesses, however, the requirements for the geometry, the stability and the abrasion resistance of the tip increase. In particular, in the case of recesses with a high aspect ratio, i.e., a high ratio between the depth and the lateral dimensions, the geometry of the tip and its manufacturability become increasingly critical. As a consequence, recesses with a high aspect ratio may not be sufficiently characterized by using an atomic force microscope.

SUMMARY OF THE INVENTION

One aspect of the present invention provides an improved method for characterizing a recess located on a surface of a substrate in a non-destructive, accurate and reliable manner.

Another aspect of the present invention provides an improved method for characterizing the depth of a recess located on a surface of a substrate, which may be applied to a recess with a high aspect ratio in particular.

Another aspect of the present invention provides an improved method for detecting an insulating layer at the bottom of a recess located on a surface of a substrate.

A further aspect of the present invention provides an improved device for characterizing a recess located on a surface of a substrate in a non-destructive, accurate and reliable manner.

According to one aspect of the present invention, a method for characterizing a recess located on a surface of a substrate is provided. In a first step, a measurement tip is positioned directly above the recess. Thereafter, an electrically conductive path is provided between the measurement tip and the bottom of the recess by ionizing a medium located in the recess. A voltage is applied between the measurement tip and the substrate to measure a current flowing between the measurement tip and the bottom of the recess. Finally, the recess is characterized on the basis of the magnitude of the measured current.

This method makes it possible to characterize a recess located on a surface of a substrate in a non-destructive, accurate and reliable manner. The requirements of the method include that a medium located in the recess, e.g., air, may be ionized to provide the electrically conductive path, and that the substrate, the surface or a surface area of the substrate to which the voltage is applied to comprise an electrically conductive material to provide a current flowing along the electrically conductive path between the measurement tip and the bottom of the recess. Since the measurement tip is not inserted into the recess of interest, no problems with regard to the geometry and the manufacturability of the measurement tip arise. As a consequence, the method may be applied to a recess with a high aspect ratio, in particular.

In one embodiment of the present invention, the measurement tip is positioned above the recess by using an atomic force microscope. As described above, an atomic force microscope may be utilized to derive information on the topography of a surface and thus on the exact position and the lateral dimensions of the recess of interest. Consequently, the measurement tip may be positioned directly above the recess with a high accuracy.

In another embodiment of the present invention, the measurement tip is oriented coplanar to the surface of the substrate. Consequently, the current flows along the electrically conductive path provided between the top and the bottom of the recess. Because this distance corresponds to the depth of the recess, an exact characterization of the recess on the basis of the magnitude of the measured current is possible.

In another embodiment of the present invention, the measurement tip is positioned directly above a center area of the recess and the medium is ionized within the center area of the recess. Thus, an electrically conductive path between the measurement tip and a sidewall of the recess, which would lead to a false characterization of the recess, is prevented.

In yet another embodiment of the present invention, the medium located in the recess is ionized by exposing the same to an alpha ray source, e.g., an Americium source. In contrast to a beta ray source, for example, an alpha ray source emits a relatively weak radiation which does not risk damaging the surface of the substrate.

According to another aspect of the present invention, a method for characterizing the depth of a recess located on a surface of a substrate is provided. In a first step, a measurement tip is positioned directly above the recess. Afterwards, an electrically conductive path is provided between the measurement tip and the bottom of the recess by ionizing a medium located in the recess. A voltage is applied between the measurement tip and the substrate to measure a current flowing between the measurement tip and the bottom of the recess. Finally, the depth of the recess is characterized on the basis of the magnitude of the measured current.

This method makes it possible to characterize the depth of a recess located on a surface of a substrate in a non-destructive, accurate and reliable manner. The method is based on the fact that the current flowing between the measurement tip and the bottom of the recess is dependant, amongst other things, on the depth of the recess. In particular, the magnitude of the current is inversely proportional to the distance between the measurement tip and the bottom of the recess. Consequently, the magnitude of the measured current may be utilized to characterize the depth of the recess. Moreover, the method may be applied particularly to a recess with a high aspect ratio as the measurement tip is not inserted into the recess.

In one embodiment of the present invention, the method further comprises calibrating the measured current by performing an equivalent measurement of the current flowing between the measurement tip and the bottom of a reference recess of known depth. To control the stability of the electrically conductive path, this calibration measurement may be repeated, e.g., at a given frequency.

Due to the fact that the current may be reduced or eliminated by an insulating layer located at the bottom of the recess, thus potentially limiting the accuracy of the inventive method, another embodiment of the present invention further comprises cleaning the bottom of the recess by applying an etch process prior to said step of positioning the measurement tip above the recess.

According to another aspect of the present invention, a method for detecting an insulating layer at the bottom of a recess located on a surface of a substrate is provided. In a first step, a measurement tip is positioned directly above the recess. Thereafter, an electrically conductive path is provided between the measurement tip and the bottom of the recess by ionizing a medium located in the recess. A voltage is applied between the measurement tip and the substrate to measure a current flowing between the measurement tip and the bottom of the recess. Finally, an insulating layer is detected at the bottom of the recess on the basis of the magnitude of the measured current.

This method allows detecting an insulating layer located at the bottom of a recess in a non-destructive and reliable manner. Such an insulating layer represents, e.g., a residue layer left at the bottom of the recess due to an incomplete etch process of the recess. The method is based on the fact that an insulating layer reduces or even prevents a current flowing between the measurement tip and the bottom of the recess, as described above. Consequently, the magnitude of the measured current may be utilized to detect such an insulating layer.

In one embodiment of the present invention, the method further comprises performing an equivalent measurement of the current flowing between the measurement tip and the bottom of a reference recess having no insulating layer at the bottom and comparing the magnitudes of the measured currents. In this embodiment, a difference between the magnitudes of the measured currents may be utilized as an indication for an insulating layer located at the bottom of the recess of interest.

According to another aspect of the present invention, a device for characterizing a recess located on a surface of a substrate is provided. This device comprises a measurement tip, a positioning unit for positioning the measurement tip directly above the recess, a radiation source for ionizing a medium located in the recess to provide an electrically conductive path between the measurement tip and the bottom of the recess, a voltage source for applying a voltage between the measurement tip and the substrate, a current measuring unit for measuring a current flowing between the measurement tip and the bottom of the recess, and an evaluation unit for characterizing the recess on the basis of the magnitude of the measured current.

According to the inventive method described above, this device makes it possible to characterize a recess located on a surface of a substrate in a non-destructive, accurate and reliable manner. Due to the fact that the measurement tip is only positioned above the recess and not inserted into the recess, the device may be utilized in particular to characterize a recess with a high aspect ratio.

In one embodiment of the present invention, the positioning unit is an atomic force microscope comprising a microscope tip for locating the recess, the microscope tip being fixed to a cantilever. As described above, the usage of an atomic force microscope particularly allows deriving information on a topography of the surface and thus on the exact location and the lateral dimensions of the recess of interest. As a consequence, the measurement tip may be positioned directly above the recess with a high accuracy.

In yet another embodiment of the present invention, the microscope tip of the atomic force microscope is the measurement tip.

BRIEF DESCRIPTION OF THE DRAWINGS

These and other aspects and features of the present invention will become clear from the following description taken in conjunction with the accompanying drawings in which.

DETAILED DESCRIPTION OF THE PREFERRED EMBODIMENT

Figure 1:
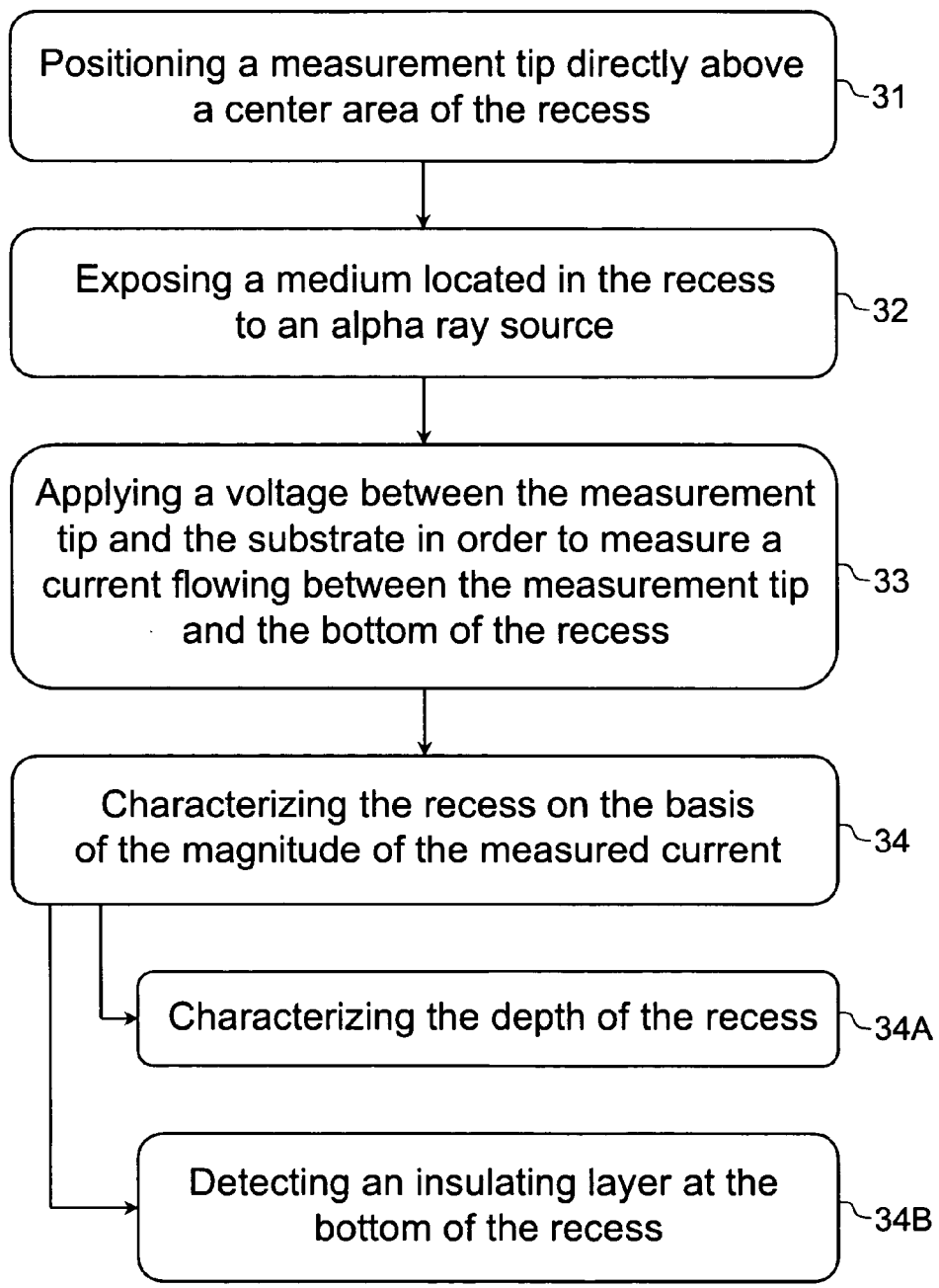
FIG. 1 is a flow chart of a method for characterizing a recess located on a surface of a substrate according to one embodiment of the present invention.

FIG. 1 shows a flow chart of a method for characterizing a recess located on a surface of a substrate according to one embodiment of the present invention. This method allows a characterization of a recess in a non-destructive, accurate and reliable manner and may be applied to a recess with a high aspect ratio, in particular. The application of the method requires that the substrate, the surface or a surface area of the substrate comprise an electrically conductive material. The substrate may be a semiconductor wafer, for example, wherein the recess is produced by subjecting the wafer to specific photolithographic and etch processes.

In a first step 31, a measurement tip is positioned directly above a center area of the recess, wherein the measurement tip is oriented coplanar to the surface of the substrate. To locate the recess of interest and to position the measurement tip above the center area of the recess with a high accuracy, step 31 may be performed utilizing an atomic force microscope. More specifically, positioning of the measurement tip above the recess may be performed utilizing a standard tapping mode of the atomic force microscope, which will be described later with reference to FIG. 2.

In a subsequent step 32, a medium located in the recess is exposed to an alpha ray source, e.g., an Americium source, to ionize the medium within the center area of the recess. Consequently, an electrically conductive path is provided between the measurement tip and the bottom of the recess, which extends within the center area of the recess. In general, air surrounding the substrate and thus located in the recess is considered to be utilized as a medium. Alternatively, other gases or substances may be utilized if they may be ionized by the radiation emitted from an alpha ray source.

Instead of utilizing an alpha ray source, other radiation sources such as a beta ray source might be utilized to ionize the medium located in the recess. However, the usage of an alpha ray source is preferred since the radiation emitted from an alpha ray source is relatively weak such that damages to the surface of the substrate and the recess due to the radiation do not occur.

A voltage is applied between the measurement tip and the substrate in a step 33 to measure a current flowing between the measurement tip and the bottom of the recess.

Due to the fact that the measurement tip is positioned directly above the center area of the recess and that the electrically conductive path extends within the center area of the recess, the current flows accordingly within the center area of the recess. In addition, the measurement tip is oriented coplanar to the surface of the substrate and thus with the top of the recess. As a consequence, the current flows along the electrically conductive path provided between the top and the bottom of the recess. This distance corresponds to the depth of the recess.

In a subsequent step 34, the recess is characterized on the basis of the magnitude of the measured current. Since the magnitude of the current is inversely proportional to the distance between the measurement tip and the bottom of the recess, the magnitude of the measured current may be utilized to characterize the depth of the recess (step 34A).

This characterization of the depth of the recess may be performed with a high accuracy as the current flows within the center area of the recess and thus not from the measurement tip towards a sidewall of the recess, which would lead to a false characterization of the depth. Moreover, it is advantageous that the measurement tip is oriented coplanar to the surface of the substrate and thus with the top of the recess such that the magnitude of the measured current is inversely proportional to the depth of the recess.

The current is further dependant on the applied voltage between the measurement tip and the substrate and also on the resistance or the conductance of the electrically conductive path provided between the measurement tip and the bottom of the recess. The conductance of the electrically conductive path is furthermore a function of the strength of the alpha ray source and of the properties of the ionized medium located in the recess.

In one embodiment, the measured current is calibrated by performing an-in situ measurement of the current flowing between the measurement tip and the bottom of a reference recess of known depth at equal conditions. Due to the fact that the strength of the alpha ray source and/or the properties of the medium might fluctuate, thus influencing the measurement, this calibration step may be repeated several times, for example, at a given frequency. As a consequence, such fluctuations may be detected and furthermore leveled out to characterize the depth of the recess with a high accuracy. To avoid property fluctuations of the medium, a stable atmosphere may be maintained in the measurement chamber where the inventive method depicted in FIG. 1 is performed.

A characterization of the depth of the recess on the basis of the magnitude of the measured current, however, may be restricted by an insulating layer located at the bottom of the recess. Such a layer (e.g., a residue layer remaining at the bottom of the recess because of an insufficient etch process utilized to fabricate the recess) may reduce or even prevent a current flowing between the measurement tip and the bottom of the recess. Consequently, an additional step may be performed to clean the bottom of the recess by applying an etch process, e.g., a wet or a dry etch process to remove such an insulating layer, prior to the step of positioning the measurement tip above the recess.

On the contrary, the magnitude of the measured current may also be utilized to detect an insulating layer at the bottom of the recess (step 34B). A magnitude of the measured current of about zero or a magnitude of the current which is clearly smaller in comparison to an expected magnitude of the current may for example be utilized as an indication for an insulating layer located at the bottom of the recess.

To detect an insulating layer at the bottom of the recess, the further steps of performing an equivalent measurement of the current flowing between the measurement tip and the bottom of a reference recess having no insulating layer at the bottom and comparing the magnitudes of the measured currents may be performed. Consequently, a difference between the magnitudes of the measured currents may be utilized as an indication for an insulating layer at the bottom of the recess of interest.

Moreover, the method may also include performing the aforesaid additional step of cleaning the bottom of the recess by applying an etch process at first and subsequently to perform the described steps for detecting an insulating layer located at the bottom of the recess. As a consequence, the quality of this additional cleaning process may be evaluated.

Figure 2:
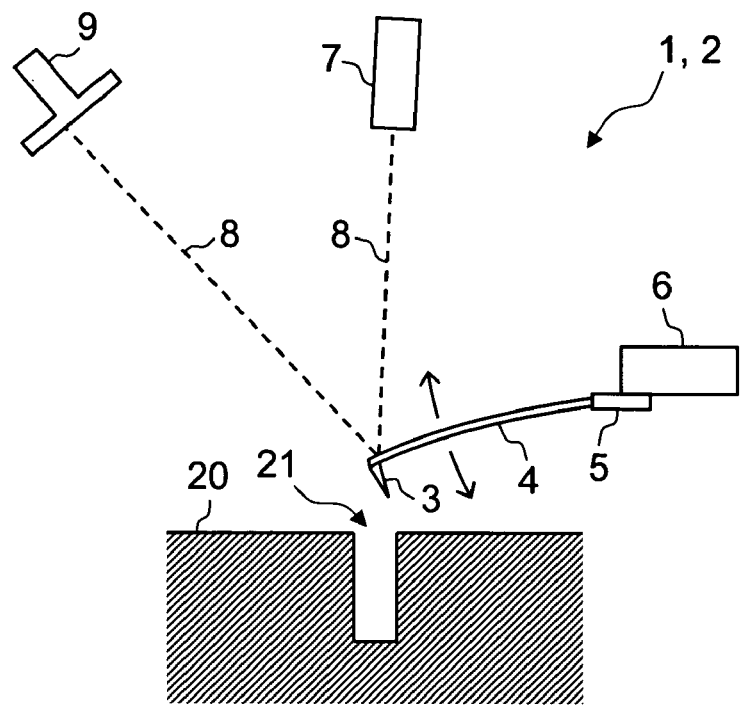
FIGS. 2 and 3 are schematic views of a device for characterizing a recess located on a surface of a substrate according to one embodiment of the present invention.
Figure 3:
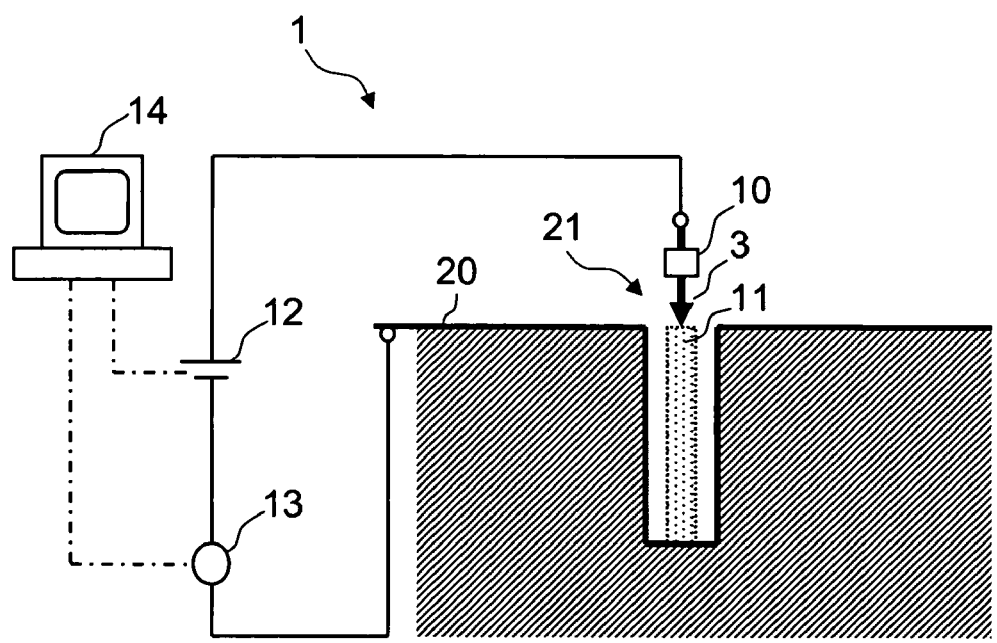

FIGS. 2 and 3 show schematic views of a device 1 for characterizing a recess 21 located on the surface of a substrate 20 according to the method described above with reference to FIG. 1. The device 1 comprises a measurement tip 3 and a positioning unit for positioning the measurement tip 3 directly above the recess 21.

FIG. 2 shows the positioning unit of the device 1 which is an atomic force microscope 2. The atomic force microscope 2 comprises a microscope tip which is the measurement tip 3. The measurement tip 3 is fixed to a cantilever 4 which is connected to a dither piezo 5 and a support 6.

To locate the recess 21, the atomic force microscope 2 may be operated in the so-called tapping mode. For this, the dither piezo 5 induces a periodic deflection to the cantilever 4 to oscillate the cantilever 4 at or near its resonant frequency. The oscillating cantilever 4 is positioned above the surface of interest so that the tip 3 only taps the surface for a very small fraction of its oscillation period.

The periodic deflection of the cantilever 4 is monitored by reflecting a laser beam 8 emitted from a laser 7 from a backside of the cantilever 4 and onto a position sensitive photodetector 9. As the tip 3 approaches the surface of interest, the amplitude of the cantilever deflection changes due to interatomic interactions between the measurement tip 3 and the surface. This amplitude change is utilized as a feedback signal to decipher the topography of the surface. In this manner, the exact position and lateral dimensions of the recess 21 may be obtained to position the measurement tip 3 directly above a center area of the recess 21.

Instead of monitoring the periodic deflection of the cantilever 4 with a laser beam reflection, other techniques such as piezoelectric or interferometric techniques may be utilized. Moreover, the atomic force microscope 2 may also be operated in other modes different from the tapping mode such as the contact or non-contact mode to locate the recess 21 of interest.

FIG. 3 shows the device 1 after positioning the measurement tip 3 directly above the center area of the recess 21, wherein the measurement tip 3 is oriented coplanar to the surface of the substrate 20. At this position, the forced oscillation of the cantilever 4 and the measurement tip 3 is suspended.

As shown in FIG. 3, the device 1 further comprises an electrically isolated alpha ray source 10 for ionizing a medium located in the recess 21. Consequently, an electrically conductive path 11 is provided between the measurement tip 3 and the bottom of the recess 21. Since the alpha ray source 10 is mounted directly above the measurement tip 3, the electrically conductive path 11 only extends within the center area of the recess 21 and not towards a sidewall of the recess 21.

The device 1 further comprises a voltage source 12 for applying a DC voltage between the measurement tip 3 and the substrate 20 or the surface or a surface area of the substrate 20. As a consequence, a current flows along the electrically conductive path 11 provided between the measurement tip 3 and the bottom of the recess 21 and thus within the center area of the recess 21. Due to the fact that the measurement tip 3 is oriented coplanar to the surface of the substrate 20 and thus with the top of the recess 21, the current flows from the top of the recess 21 to the bottom of the same. This distance corresponds to the depth of the recess.

The magnitude of the current may be measured by an Ampere meter 13. Furthermore, the device 1 comprises an evaluation unit 14 for characterizing the recess 21 on the basis of the magnitude of the measured current.

While the present invention has been described in terms of specific embodiments, it is evident in view of the foregoing description that various variations and modifications may be carried out without departing from the scope of the invention.

As an example, the device 1 may comprise an atomic force microscope having a dual tip configuration, i.e., utilizing one tip as a measurement tip for measuring a current flowing along an electrically conductive path provided between the measurement tip and the bottom of a recess of interest and utilizing a second tip as a microscope tip for locating the recess in advance and for positioning the measurement tip directly above the recess. Such a dual tip configuration has the advantage of avoiding or minimizing manufacturing tolerances and in particular usage-induced changes to the measurement tip geometry.

Other possible variations include, for example, devices comprising positioning units different from an atomic force microscope.

While the foregoing is directed to embodiments of the present invention, other and further embodiments of the invention may be devised without departing from the basic scope thereof, and the scope thereof is determined by the claims that follow.

What is claimed is:

1. A method for characterizing a recess located on a surface of a substrate, comprising:
    positioning a measurement tip above the recess;
    ionizing a medium located in the recess to provide an electrically conductive path between the measurement tip and a bottom of the recess;
    applying a voltage between the measurement tip and the substrate;
    measuring a current flowing between the measurement tip and the bottom of the recess; and
    characterizing the recess based on a magnitude of the measured current.

2. The method of claim 1, wherein the measurement tip is positioned centrally above the recess utilizing an atomic force microscope.

3. The method of claim 2, wherein the measurement tip is positioned above the recess utilizing tapping mode atomic force microscopy technique.

4. The method of claim 2, further comprising:
    utilizing a second tip of the atomic force microscope to locate the recess on the surface of the substrate and to position the measurement tip.

5. The method of claim 1, wherein the measurement tip is oriented coplanar to the surface of the substrate.

6. The method of claim 1, wherein the measurement tip is positioned directly above a center area of the recess and the medium is ionized within the center area of the recess.

7. The method of claim 1, wherein the medium located in the recess is ionized by exposure to an alpha ray source.

8. The method of claim 1, wherein a depth of the recess is characterized based on the magnitude of the measured current.

9. The method of claim 8, further comprising:
    calibrating the measured current by performing a calibration current measurement between the measurement tip and a reference recess bottom having a known depth.

10. The method of claim 9, wherein the calibrating step and the measuring step are performed with equivalent chamber conditions.

11. The method of claim 8, further comprising:
    prior to positioning the measurement tip above the recess, cleaning the bottom of the recess by applying an etch process.

12. The method of claim 1, wherein an insulating layer at the bottom of the recess is detected based on the magnitude of the measured current.

13. The method of claim 12, further comprising:
performing a reference current measurement between the measurement tip and a reference recess bottom having known depth and no insulating layer; and
comparing the measured current and the reference current measurement.

14. The method of claim 12, further comprising:
prior to positioning the measurement tip above the recess, cleaning the bottom of the recess by applying an etch process.

15. The method of claim 14, further comprising:
determining an effectiveness of the etch process based on the magnitude of the measured current.

16. An apparatus for characterizing a recess located on a surface of a substrate, comprising:
a measurement tip;
a positioning unit for positioning the measurement tip directly above the recess;
a radiation source for ionizing a medium located in the recess to provide an electrically conductive path between the measurement tip and the bottom of the recess;
a voltage source for applying a voltage between the measurement tip and the substrate;
a current measuring unit for measuring a current flowing between the measurement tip and the bottom of the recess; and
an evaluation unit for characterizing the recess based on a magnitude of the measured current.

17. The apparatus of claim 16, wherein the positioning unit comprises an atomic force microscope having a microscope tip for locating the recess and a cantilever connected to the microscope tip.

18. The apparatus of claim 17, wherein the microscope tip is the measurement tip.

19. The apparatus of claim 17, wherein the atomic force microscope comprises a first tip configured as the measurement tip and a second tip configured to locate the recess and to position the first tip directly above the located recess.

20. The apparatus of claim 16, wherein the radiation source is disposed on the measurement tip.

21. The apparatus of claim 16, wherein the radiation source comprises an alpha ray source.

22. A method for characterizing a recess located on a surface of a substrate, comprising:
positioning a measurement tip of an atomic force microscope above a central area of the recess and coplanar to the surface of the substrate;
ionizing a medium located in the recess;
applying a voltage between the measurement tip and a bottom of the recess;
measuring a current flowing between the measurement tip and the bottom of the recess; and
characterizing the recess based on a magnitude of the measured current, wherein at least one of a depth of the recess and an insulating layer disposed at the bottom of the recess is characterized.

23. The method of claim 22, further comprising:
utilizing a second tip of the atomic force microscope to locate the recess on the surface of the substrate and to position the measurement tip.

24. The method of claim 22, further comprising:
prior to positioning the measurement tip above the recess, cleaning the bottom of the recess by applying an etch process.

25. The method of claim 24, further comprising:
performing a reference current measurement between the measurement tip and a reference recess bottom having known depth and no insulating layer, under equivalent chamber conditions; and
comparing the measured current and the reference current measurement.

* * * * *